United States Patent [19]

Heuer et al.

[11] Patent Number: 5,703,103
[45] Date of Patent: Dec. 30, 1997

[54] THIAZOLYLPYRAZOLINONES AND THEIR USE FOR PROTECTING TECHNICAL MATERIALS

[75] Inventors: Lutz Heuer, Krefeld; Peter Wachtler, Köln; Martin Kugler, Leichlingen; Heinrich Schrage, Krefeld; Klaus Sasse, Bergisch Gladbach, all of Germany

[73] Assignee: Bayer Aktiengesellschaft, Leverkusen, Germany

[21] Appl. No.: 716,239

[22] PCT Filed: Mar. 20, 1995

[86] PCT No.: PCT/EP95/01032

§ 371 Date: Sep. 24, 1996

§ 102(e) Date: Sep. 24, 1996

[87] PCT Pub. No.: WO95/26962

PCT Pub. Date: Oct. 12, 1995

[30] Foreign Application Priority Data

Mar. 31, 1994 [DE] Germany .................. 44 11 235.1

[51] Int. Cl.$^6$ .................. A01N 43/78; C07D 417/04

[52] U.S. Cl. .................. 514/365; 548/204; 548/205; 106/14.16; 106/18.33

[58] Field of Search .................. 548/204, 205; 514/365

[56] References Cited

PUBLICATIONS

Singh et al, Chemical Abstracts, vol. 120, No. 32 3362 (1994).
Indian J. Heterocycl. Chem 3(1), 5–8 (1993).
Singh et al, Chemical Abstracts, vol. 120, No. 8516g (1994).
Sawhney et al, Chemical Abstracts, vol. 98, No. 125958y (1983).
Richter et al, Chemical Abstracts, vol. 96, No. 52303c (1982).

*Primary Examiner*—Robert W. Ramsuer
*Attorney, Agent, or Firm*—Sprung Kramer Schaefer & Briscoe

[57] ABSTRACT

The present invention relates to novel thiazolylpyrazolinones, a process for their preparation and their use for the protection of technical materials.

7 Claims, No Drawings

THIAZOLYLPYRAZOLINONES AND THEIR USE FOR PROTECTING TECHNICAL MATERIALS

This application is a 371 of PCT/EP96/01032 filed Mar. 20, 1995.

The present invention relates to novel thiazolylpyrazolinones, a process for their preparation and their use for the protection of technical materials.

Thiazolylpyrazolinones are known and are described, e.g., in JP-2 149 617, Indian, J. Chem. 21 B, 869 (1982), Synth. Com. 23, 1855 (1993), J. heterocyclic Chem. 27, 865 (1990) and DD-150 203. However, their use for the protection of industrial materials has not been disclosed.

The application relates to novel thiazolylpyrazolinone derivatives of the formula

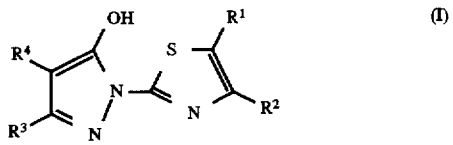

in which $R^1$, $R^2$, $R^3$ independently of each other each represent hydrogen, alkyl or halogen, and $R^4$ represents hydrogen or unsubstituted or substituted alkyl, alkenyl, alkinyl, cycloalkyl, cycloalkenyl, alkyl (cycloalkyl), alkenyl (cycloalkenyl), alkoxy, alkylthio, aralkoxy, aralkylthio, aralkyl, aryl, hetaryl, aryloxy, hetaryloxy, arylthio, hetarylthio, alkoxycarbonyl, alkoxycarbonalalkyl or cyanoalkyl, or their acid addition products or metal salt complexes.

In the present application:

Alkyl preferably denotes straight-chain or branched, unsubstituted or substituted alkyl having 1 to 18 C atoms, such as Me, Et, n-, i-propyl, n-, i-, s- and tert-butyl, n-, i- and tert-pentyl, n-hexyl, n-octyl, n-nonyl, n-decyl, n-undecyl, n-dodecyl, n-tridecyl, n-tetrad ecyl, n-pentadecyl, n-hexadecyl, n-heptodecyl or n-octadecyl or their branched structural isomers.

Suitable substituents are preferably halogen, such as chlorine and/or fluorine.

An alkyl radical can also be interrupted by 1 to 2 heteroatoms such as oxygen or sulphur, or atom groups such as N-Me, N-Et, —S(O), —SO₂, without the total number of atoms changing.

Alkenyl (+alkinyl) is preferably defined as alkyl, changed only to the extent that at least one and at most three C—C single bonds have been replaced by a C—C double (triple) bond. The number of C atoms is at least three and is increased by at least two C atoms with each further double bond (triple bond) which is added.

Cycloalkyl and cycloalkenyl groups include cycloalkyl having preferably 3 (5) to 7 C atoms, such as cyclopropyl, cyclobutyl, cycloheptyl, cyclopentyl, cyclopentenyl, cyclohexenyl, cyclohexyl; preferred substituted cycloalkyl groups include cycloalkyl substituted by 1 to 3 $C_1$–$C_4$-alkyl groups or 1 to 3 halogen atoms, such as chlorine and/or fluorine, such as methylcyclohexyl, dimethylcyclohexyl, 1,3,3-trimethylcyclohexyl, 3-chlorocyclohexyl. Alkyl (cycloalkyl) (and alkyl(cycloalkenyl) groups) preferably contain 1 to 6 C atoms in the straight-chain or branched alkyl moiety and 3 (5) to 7 atoms in the cycloalkyl/alkenyl moiety; particularly (1-cyclopentyl)methyl, (1-cyclopentenyl) methyl, (1-cyclohexenyl)methyl, (1-cyclohexyl)methyl, (1-cyclopropyl)methyl.

Alkoxycarbonyl represents straight-chain or branched alkoxycarbonyl preferably having 1 to 6 C atoms in the alkoxy radical, such as methoxycarbonyl, ethoxycarbonyl, n- and i-propoxycarbonyl, n-, i-, sec- and tert-butoxycarbonyl, hexoxycarbonyl. Analogous meanings apply to the alkoxycarbonylalkyl groups.

Aralkyl preferably contains 1 to 6, in particular 1 to 4, C atoms in the straight-chain or branched alkyl moiety and preferably contains phenyl or naphthyl as aryl moiety.

Examples of aralkyl groups of this type include benzyl, α-methyl benzyl, α,α-dimethylbenzyl, 2-phenethyl, α- and β-naphthylmethyl. These aralkyl radicals can bear 1 to 3 substituents selected from the group consisting of halogen (in particular chlorine and/or fluorine), nitro, cyano, nonhalogenated or halogenated $C_1$–$C_4$-alkyl or -alkoxy, such as methyl, ethyl, trifluoromethyl, difluorochloromethyl, difluoromethyl, trichloromethyl, methoxy, ethoxy, trifluoromethoxy, difluorochloromethoxy and difluoromethoxy, non-halogenated or halogenated $C_1$–$C_4$-alkylmercapto, such as methylmercapto, trifluoromethylmercapto, difluorochloromethylmercapto.

The term aryl is to be taken to mean unsubstituted or substituted aryl preferably having 6 to 12 C atoms in the aryl moiety. Preferred examples include phenyl, biphenyl and naphthyl. The aryl groups can bear 1 to 3 substituents selected from the group consisting of halogen (in particular chlorine and/or fluorine), $C_1$–$C_6$-alkyl, -alkoxy or thioalkoxy, halogen-$C_1$–$C_2$-alkyl (such as trifluoromethyl, difluoromethyl), cyano, nitro, $C_1$–$C_6$-alkoxycarbonyl or amino.

The term alkoxy is to be taken to mean straight-chain and branched alkoxy preferably having 1 to 12, in particular 1 to 4, C atoms. Preferred examples include methoxy, ethoxy, n- and i-propoxy, n-, i-, sec- and ter-butoxy, pentoxy, hexoxy, heptoxy, octoxy, nonoxy and decoxy. The alkoxy groups can be substituted by 1 to 3 halogen atoms (Cl, F), preferably: O—CF₃, O—CHF₂, O—CF₂, O—CF₂—O, O—CF₂—CF₂—O.

Alkylthio represents straight-chain or branched alkylthio preferably having 1 to 12 C atoms. Preferred examples include methylthio, ethylthio, n- and i-propylthio, n-, i-, sec- and ter-butylthio, n-pentylthio and its isomers such as 1-, 2- and 3-methylbutylthio. The alkylthio groups can be substituted by 1 to 3 halogen atoms (preferably chlorine and/or fluorine); preferred examples of this are di- and trifluoromethylthio and difluorochloromethylthio.

Aralkoxy preferably contains 1 to 6 C atoms in the straight-chain or branched alkyl moiety and preferably contains phenyl as aryl moiety. Preferred examples are benzyloxy and phenethyloxy. The aralkoxy groups can be substituted by 1 to 3 halogen atoms (preferably chlorine and/or fluorine) or by a $C_1$–$C_4$-alkyl group.

Cyanoalkyl has alkyl (1 to 6) only substituted with cyano, preferably terminally.

Hetaryl: furanyl, thienyl, thiazolyl, pyrazolyl, pyrrolyl, imidazyl, triazolyl, with or without 1 to 2 halogen or alkyl, alkoxy or thioalkoxy substituents.

Halogen: F, Cl, Br, I.

Aralkylthio preferably contains 1 to 6 C atoms in the straight-chain or branched alkyl moiety and preferably contains phenyl as aryl moiety. A preferred example is benzylthio. The aralkylthio groups can be substituted by 1 to 3 halogen atoms (preferably chlorine and/or fluorine) or by a $C_1$–$C_4$-alkyl group.

Aryloxy preferably contains 1 to 10 C atoms in the aryl moiety. Preferred examples are phenoxy and naphthoxy. The aryloxy groups can bear 1 to 3 substituents selected from the group consisting of halogen (preferably chlorine and/or fluorine), $C_1$–$C_4$-alkyl, halogeno-$C_1$–$C_2$-alkyl (such as di- and trifluoromethyl), cyano, nitro or amino.

Arylthio preferably contains 6 to 10 C atoms in the aryl moiety. Preferred examples are phenylthio and naphthylthio. The arylthio groups can bear the substituents listed under "aryloxy".

Preferred compounds for 1,ω-$C_3$–$C_6$-alk(en)ylene radicals include 1,3-propylene, 1,4-butylene and 1,4-butadiene (1,3) ylene.

Compounds of the formula (I),

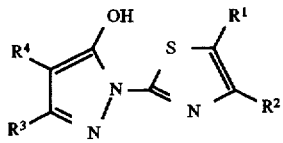

in which $R^1$, $R^2$, $R^3$ denote hydrogen or methyl,
$R^4$ denotes unsubstituted or substituted alkyl, cycloalkyl, alkenyl, aralkyl or aryl, are preferred.

Compounds of the formula (I), in which $R^1$ denotes hydrogen,
$R^2$, $R^3$ denote hydrogen or methyl,
$R^4$ denotes unsubstituted or substituted alkyl, cycloalkyl, aralkyl or aryl, are particularly preferred.

Compounds of the formula (I), in which $R^1$, $R^2$ and $R^3$ denote hydrogen,
$R^4$ denotes unsubstituted or substituted alkyl or cycloalkyl, are very particularly preferred.

The compounds of the invention of the formula (I) can be present as various (see below) tautomers, inter alia, also, in their tautomeric pyrazol-5-one form.

The novel thiazolylpyrazolinone derivatives of the formula (I) are obtained by reacting thiocarbamoyl compounds of the formula (II)

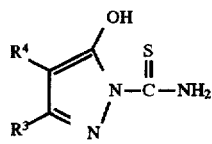

in which $R^3$ and $R^4$ have the meanings given above, in the presence or absence of a solvent or diluent and in the presence or absence of a base, with compounds of the formula (III)

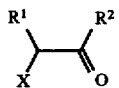

in which $R^1$ and $R^2$ have the meanings given above and X represents a leaving group.

The thiocarbamoyl pyrazolones of the formula (II) and the process for their preparation are known and are described, e.g., in JP-79/115 374, JP-79/119 031, J. Pesticide, Sci. 11, 205–212 (1986), Arch. Pharm. 316 (1983) 2–6, Sci. Pharm. 51 (2) (1982) 167–172 and EP-1 515 934.

The compounds of the formula (II) are conventionally obtained by reacting corresponding α-formylacetic esters or α-formylacetamide or β-ketoacetic esters or a β-ketoacetamide with unsubstituted or substituted thiosemicarbazide. The formyl acid esters to be used are obtained by various ways disclosed in the literature, thus, e.g., by analogy with the method described in EP 417 597 or DE 2 643 205 of hydroformylation of α,β-unsaturated esters.

The compounds of the formula (III) are likewise known or are obtainable by generally known methods.

To facilitate the ring closure reactions, bases such as sodium hydroxide, potassium hydroxide or potassium tert-butylate are advantageously added. Preferably, the base is added in a roughly equivalent amount.

The processes are carried out in the presence or absence of a solvent; solvents which have proved useful are especially alcohols such as ethanol or aromatic hydrocarbons such as toluene.

The processes are is carried out within a relatively broad temperature range. For the thiosemicarbazone formation which proceeds first, temperatures of 20° to 110° C., preferably between 60° and 90° C., are employed. The cyclo-condensation reaction which proceeds after addition of base is performed at temperatures of 20° to 100° C., preferably 20° to 40° C. The compounds of the formula (II) thus obtained are then reacted with the compounds of the formula (III) at temperatures of –20° to 50° C., preferably 0° to 30° C.

The compounds of the formulae (I) and (II) can be isolated from the reaction mixtures by known methods. Generally, a procedure is followed in such a way that the reaction mixtures are freed of solvent and the residue is treated with aqueous hydrochloric acid. The compounds precipitating out in the course of this are separated off by filtering off with suction. However, it is also possible to pour the reaction mixture directly into a great excess of dilute hydrochloric acid and to filter off the compounds formed as a precipitate.

The preparation of the compounds (I) of the invention is also possible in a one-pot process without isolation of the precursor of the formula (II).

The active compounds of the formula (I) and the compositions of the invention have a powerful microbicidal action and can be used in practice to control undesirable microorganisms. The active compounds of the formula (I) and the compositions of the invention are suitable for the protection of technical materials against attack and destruction by undesirable microorganisms.

Technical materials in the present context are to be taken to mean non-living materials which have been prepared for use in engineering. For example, technical materials which are to be protected by active compounds of the invention against microbial change or destruction can be adhesives, sizes, paper and board, textiles, leather, wood, coatings and plastics, cooling lubricants and other materials which can be attacked or broken down by microorganisms. In the context of the materials to be protected, components of production plants, for example cooling water circuits, may also be mentioned, which can be adversely affected by growth of microorganisms. In the context of the present invention, technical materials which may be mentioned are preferably adhesives, sizes, papers and boards, leather, wood, coatings, cooling lubricants and heat transfer fluids, particularly preferably coatings.

Microorganisms which can break down or change the technical materials and which may be mentioned by way of example are bacteria, fungi, yeasts, algae and slime-forming organisms. Preferably, the active compounds or compositions of the invention act against fungi, in particular moulds, fungi which discolour and destroy wood (Basidiomycetes) and against slime-forming organisms and algae.

Microorganisms of the following genera may be mentioned by way of example:

Alternaria, such as *Alternaria tenuis*,
Aspergillus, such as *Aspergillus niger*,
Chaetomium, such as *Chaetomium globosum*,
Coniophora, such as *Coniophora puetana*,
Lentinus, such as *Lentinus tigrinus*,
Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*,
Staphylococcus, such as *Staphylococcus aureus*.

The active compounds of the formula (I) can, depending on their respective physical and/or chemical properties, be converted into conventional formulations, such as solutions, emulsions, suspensions, powders, foams, pastes, granules, aerosols and dust encapsulated in polymeric substances.

These formulations are prepared in a known manner, e.g. by mixing the active compounds with extenders, that is liquid solvents, pressurized liquefied gases and/or solid carriers, with or without the use of surface-active agents, that is emulsifiers and/or dispersants and/or foam-forming agents. When water is used as extender, e.g., organic solvents can also be used as cosolvents. Liquid solvents which are suitable are essentially: aromatics, such as xylene, toluene, alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, e.g. mineral oil fractions, alcohols, such as butanol or glycol or their ethers and esters, ketones, such as acetone, methyl ethyl ketone, methyl isobutyl ketone or cyclohexanone, highly polar solvents, such as dimethylformamide or dimethyl sulphoxide, and water; liquefied gaseous extenders or carriers are taken to mean those liquids which are gaseous at room temperature and at atmospheric pressure, e.g. aerosol propellant gases, such as halogenated hydrocarbons as well as butane, propane, nitrogen and carbon dioxide; solid carriers which are useful are: e.g. natural rock flours, such as kaolins, aluminas, talcum, chalk, quartz, attapulgite, montmorillonite or diatomaceous earth and synthetic rock flours, such as highly disperse silica, aluminium oxide and silicates; solid carriers for granules which are suitable are: e.g. crushed and fractionated natural rocks such as calcite, marble, pumice, sepiolite, dolomite and synthetic granules made of inorganic and organic flours and granules made of organic material such as sawdust, coconut shells, corn cobs and tobacco stalks; emulsifiers and/or foam-forming agents which are suitable are: e.g. nonionogenic and anionic emulsifiers, such as polyoxyethylene fatty acid esters, polyoxyethylene fatty alcohol ethers, e.g. alkylaryl polyglycol ethers, alkylsulphonates, alkyl sulphates, arylsulphonates and protein hydrolysates; dispersants which are suitable are: e.g. waste ligninsulphite liquors and methylcellulose.

In the formulations, deposit builders can be used, such as carboxymethylcellulose, natural and synthetic, pulverulent, granular or latex-form polymers, such as gum arabic, poly(vinyl alcohol), poly(vinyl acetate), and natural phospholipids, such as cephalins and lecithins and synthetic phospholipids. Other additives can be mineral and vegetable oils.

Colorants can be used such as inorganic pigments, e.g. iron oxide, titanium oxide, Prussian blue and organic colorants can be used, such as alizarin dyes, azo dyes and metal phthalocyanin dyes and trace nutrients can be used such as salts of iron, manganese, boron, copper, cobalt, molybdenum and zinc.

Preferably, the active compounds of the invention of the formula (I) are used to protect coatings against attack and destruction by undesirable microorganisms.

Coating in the present context is to be taken to mean a coat which is prepared from coating materials and is applied to a substrate. The coating can have penetrated into the substrate to a greater or lesser extent. It can comprise one or more layers and can be prepared by processes such as painting, spraying, immersion, flow coating or similar processes.

The compounds of the formula (I) are incorporated into the coating materials or into precursors for the preparation of the coating materials by conventional methods, e.g. by mixing the active compounds with the other components.

Coating materials of the invention therefore generally contain, in addition to at least one fungicidal active compound of the formula (I), conventional coating components in, e.g., liquid, pasty or pulverulent form, such as colorants, such as pigments or dyes, preferably pigments. Those which may be mentioned by way of example are titanium dioxide, zinc oxide and iron oxide.

Binders, such as, for example, oxidatively drying alkyd resins, vinyl polymers and vinyl copolymers, acrylic polymers and acrylic copolymers, plastic powders, novolaks, amino resins, polyester resins, epoxy resins, silicone resins, isocyanate resins; preference is given to vinyl polymers and vinyl copolymers, acrylic polymers and acrylic copolymers and other binders usable in water-dilutable coating materials.

In addition, the coatings optionally contain the following additives fillers, such as barytes, calcite, dolomite and talc, solvents, such as alcohols, ketones, esters, glycol ethers and aliphatic and aromatic hydrocarbons, and thickeners and thixotropes, dispersants and wetting agents, desiccants, skin-protecting agents, flow-control agents, antifoamers, corrosion inhibitors, UV-absorbers, perfumes, antistatic agents, antifreezes.

Coating materials or precursors for the preparation of coating materials which may be mentioned by way of example are:

sizes and adhesive based on known animal, vegetable or synthetic materials.

Plastic dispersions such as latex dispersions or dispersions based on other polymers.

Starch solutions, dispersions or slurries or other products made on a starch basis, such as printing thickeners.

Slurries of other raw materials such as colour pigments (e.g. iron oxide pigments, carbon black pigments, titanium dioxide pigments) or slurries of fillers such as kaolin or calcium carbonate.

Concrete additives, for example based on molasses or lignosulphonates.

Bitumen emulsions.

Precursors and intermediates of the chemical industry, e.g. in the production and storage of colorants.

Inks or Indian inks.

Dispersed dyes for the coating industry.

Coats and finishes.

The activity and the action spectrum of the active compounds of the formula (I) or the compositions, precursors or quite generally formulations which can be prepared therefrom can be enhanced if other antimicrobially active compounds, fungicides, bactericides, insecticides or other active compounds for enlarging the action spectrum or to achieve particular effects such as additional protection against insects are optionally added. These mixtures can have a broader action spectrum than the compounds of the invention.

In many cases synergistic effects are increased by these means, i.e. the activity of the mixture is greater than the activity of the individual components. Particularly expedient mixing partners are, e.g., the following compounds:

Triazoles, such as:

amitrole, azocyclotin, BAS 480F, bitertanol, difenoconazole, fenbuconazole, fenchlorazole, fenethanil, fluquinconazole, flusilazole, flutriafol, imibenconazole, isozofos, myclobutanil, metconazole, epoxyconazole, paclobutrazol, penconazole, propioconazole, (±)-cis-1-(4-chlorophenyl)-2-(1H-1,2,4-triazol-1-yl)-cycloheptanol, tetraconazole, triadimefon, triadimenol, triapenthenol, triflumizole, triticonazole, uniconazole and their metal salts and acid adducts.

Imidazoles such as:

imazalil, perfurazoate, prochloraz, triflumizole, 2-(1-tert-butyl)-1-(2-chlorophenyl)-3-(1,2,4-triazol-1-yl)-propan-2-ol, thiazolecarboxanilides, such as 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one and their metal salts and acid adducts.

Methyl (E)-2-[2-[6-(2-cyanophenoxy)pyrimidin-4-yloxy]phenyl]3-methoxyacrylate, methyl (E)-2-[2-[6-(2-thioamidophenoxy)pyrimidin-4-yloxy]phenyl]-3-methoxyacrylate, methyl (E)-2-[2-[6-(2-fluorophenoxy)pyrimidine-4-yloxy]phenyl]-3-methoxyacrylate, methyl (E)-2-[2-[6-(2,6-difluorophenoxy)pyrimidin-4-yloxy]phenyl]-3-methoxyacrylate, methyl (E)-2-[2-[3-(pyrimidin-2-yloxy)phenoxy]phenyl]-3-methoxyacrylate, methyl (E)-2-[2-[3-(5-methylpyrimidin-2-yloxy)-phenoxy]phenyl]-3-methoxyacrylate, methyl (E)-2-[2-[3-(phenylsulphonyloxy)phenoxy]phenyl]-3-methoxyacrylate, methyl (E)-2-[2-[3-(4-nitrophenoxy)phenoxy]phenyl]-3-methoxyacrylate, methyl (E)-2-[2-phenoxyphenyl]-3-methoxyacrylate, methyl (E)-2-[2-(3,5-dimethylbenzoyl)pyrrol-1-yl]-3-methoxyacrylate, methyl (E)-2-[2-(3-methoxyphenoxy)phenyl]-3-methoxyacrylate, methyl (E)-2-[2-(2-phenylethylen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxyphenoxy)phenyl]3-methoxyacrylate, methyl (E)-2-[2-(3-isopropyloxyphenoxy)phenyl]-3-methoxyacrylate, methyl (E)-2-[2-[3-(2-fluorophenoxy)pehnoxy]phenyl]-3-methoxyacrylate, methyl (E)-2-[2-(3-ethoxyphenoxy)phenyl]-3-methoxyacrylate, methyl (E)-2-[2-(4-tert-butylpyridin-2-yloxy)phenyl]-3-methoxyacrylate, methyl (E)-2-[2-[3-(3-cyanophenoxy)phenoxy]phenyl]-3-methoxyacrylate, methyl (E)-2-[2-(3-methhylpyridin-2-yloxymethhyl)phenyl]-3-methoxyacrylate, methyl (E)-2-[2-[6-(2-methylphenoxy)pyrimidin-4-yloxy]phenyl]-3-methoxyacrylate, methyl (E)-2-[2-(5-bromopyridin-2-yloxy-methyl)phenyl]-3-methoxyacrylate, methyl (E)-2-[2-(3-(3-iodopyridin-2-yloxy)phenoxy)phenyl]-3-methoxyacrylate, methyl (E)-2-[2-[6-(2-chloropyridin-3-yloxy)pyrimidin-4-yloxy]phenyl]-3-methoxyacrylate, (E), (E)methyl 2-[2-(5,6-dimethylpyrazin-2-ylmethyloximinomethyl)phenyl]-3-methoxyacrylate, (E)-methyl 2-{2-[6-(6-methylpyridin-2-yloxy)pyrimidin-4-yloxy]phenyl}-3-methoxyacrylate, (E),(E)-methyl 2-{2-(3-methoxyphenyl)methyloximinomethyl]phenyl}-3-methoxyacrylate, (E)methyl 2-{2-(6-(2-azidophenoxy)pyrimidin-4-yloxy]phenyl}-3-methoxyacrylate, (E),(E) methyl 2-{2-[6-phenylpyrimidin-4-yl)-methoximinomethyl]phenyl}-3-methoxyacrylate, (E),(E) methyl 2-{2-[(4-chlorophenyl)-methyloximinomethyl]phenyl}-3-methoxyacrylate, (E)methyl 2-{2-[6-(2-n-propylphenoxy)-1,3,5-triazin-4-yloxy]phenyl}-3-methoxyacrylate, (E),(E)methyl 2-{2-[(3-nitrophenyl)methyloximinomethyl]phenyl}-3-methoxyacrylate;

Succinate dehydrogenase inhibitors such as:

fenfuram, furcarbanil, cyclafluramid, furmecyclox, Seedvax, metsulfovax, pyrocarbolid, oxycarboxin, shirlan, mebenil (mepronil), benodanil, flutolanil (Moncut); naphthalene derivates such as terbinafine, naftifine, butenafine, 3-chloro-7-(2-aza-2,7,7-trimethyl-oct-3-en-5-ine);

Sulphenamides such as dichlofluanid, tolylfluanid, folpet, fluorfolpet; captan, captofol; benzimidazoles such as carbendazim, benomyl, furathiocarb, fuberidazole, thiophonatmethyl, thiabendazole or their salts;

morpholine derivatives such as tridemorph, fenpropimorph, falimorph, dimethomorph, dodemorph, aldimorph, fenpropidin and their arylsulphonic salts, such as p-toluene-sulphonic acid and p-dodecylphenyl-sulphonic acid;

dithiocarbamates, cufraneb, ferbam, mancopper, mancozeb, maneb, metam, metiram, thiram zeneb, ziram;

benzothiazoles such as 2-mercaptobenzothiazole;

benzamides such as 2,6-dichloro-N-(4-trifluoromethylbenzyl)-benzamide;

boron compounds such as boric acid, boric esters, borax; formaldehyde and compounds eliminating formaldehyde such as benzyl alcohol mono(poly)hemiformal, oxazolidines, hexa-hydro-S-triazines, N-methylol chloracetamide, paraformadehyde, nitropyrin, oxolinic acid, tecloftalam;

tris-N-(cyclhexyldiazeniumdioxy)-aluminium,N-(cyclohexyldiazeniumdioxy)-tributyl-tin or K salts, bis-N-cyclohexyldiazeniumdioxy)-copper;

N-methylisothiazolin-3-one, 5-chloro-N-methylisothiazolin-3-on, 4,5-dichloro-N-octyl-isothiazolin-3-one, N-octyl-isothiazolin-3-one, 4,5-trimethylene-isothiazolinones, 4,5-benzisothiazolinones, N-methylol chloracetamide;

aldehydes such as cinnamaldehyde, formaldehyde, glutaric dialdehyde, β-bromo-cinnamaldehyde;

thiocyanates such as thiocyanatomethylthiobenzothiazole, methylenebisthiocyanate, etc.;

quaternary ammonium compounds such as benzyldimethyltetradecylammonium chloride, benzyldimethyldodecylammonium chloride, didecyldimethaylammonium chloride; iodine derivatives, such as diiodomethyl-p-tolylsulphone, 3-iodo-2-propinyl alcohol, 4-chlorophenyl-3-iodopropargylformal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexylcarbamate, 3-iodo-2-propinyl phenylcarbamate;

phenol derivatives, such as tribromophenol, tetrachlorophenol, 3-methyl-4-chlorophenol, 3,5-dimethyl-4-chlorophenol, phenoxyethanol, dichlorophen, o-phenylphenol, m-phenylphenol, p-phenylphenol, 2-benzyl-4-chlorophenol and their alkali metal salts and earth metal salts;

microbicides having an activated halogen group such as chloroacetamide, bronopol, bronidox, tectamers such as 2-bromo-2-nitro-1,3-propanediol, 2-bromo-4'-hydroxyacetophenone, 2,2-dibromo-3-nitrile-propionamide, 1,2-dibromo-2,4-dicyanobutan, β-bromo-β-nitrostyrene;

pyridines, such as 1-hydroxy-2-pyridinethione (and their Na, Fe, Mn and Zn salts), tetrachloro-4-methylsulphonylpyridine, pyrimethanol, mepanipyrim, dipyrithion, 1-hydroxy-4-methyl-6-(2,4,4-trimethylpentyl)-2(1H)-pyridin;

metal soaps, such as tin naphthenate, copper naphthenate, zinc naphthenate, tin octoate, copper octoate, zinc octoate, tin 2-ethylhexanoate, copper 2-ethylhexanoate, zinc 2-ethylhexanoate, tin oleate, copper oleate, zinc oleate, tin phosphate, copper phosphate, zinc phosphate, tin benzoate, copper benzoate and zinc benzoate;

metal salts, such as copper hydroxycarbonate, sodium dichromate, potassium dichromate, potassium chromate, copper sulphate, copper chloride, copper borate, zinc fluorosilicate, copper fluorosilicate;

oxides, such as tributyltin oxide, $Cu_2O$, $CuO$, $ZnO$;

dialkyldithiocarbamates, such as Na and Zn salts of dialkyldithiocarbamates, tetramethylthiuram disulphide, potassium N-methyl-dithiocarbamate;

nitriles such as 2,4,5,6-tetrachloroisophthalodinitrile, disodium cyano-dithioimidocarbamate;

quinolines, such as 8-hydroxyquinolin and their Cu salts; mucochloric acid, 5-hydroxy-2(5H)-furanone;

4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazin-2-thione, N-(2-p-chlorobenzoylethyl)-hexaminium chloride, potassium N-hydroxymethyl-N'-methyl-dithiocarbamate, 2-oxo-2-(4-hydroxy-phenyl)acetohydroxycinnamoyl chloride, phenyl 2-chlorocyanovinyl sulphone, phenyl 1,2-dichloro-2-cyano-vinyl sulphone;

Ag, Zn or Cu-containing zeolites, alone or incorporated into polymeric material.

Very particular preference is given to mixtures containing azaconazole, bromuconazole, cyproconazole, dichlobutrazol, diniconazole, hexaconazole, metconazole, penconazole, propiconazole, tebuconazole, methyl (E)-methoximino[α-(o-tolyloxy)-o-tolyl)]-acetate, methyl (E)-2-{2-[6-(2-cyanophenoxy)-pyrimidin-4-yl-oxy]phenyl}-3-methoxyacrylate, methfuroxam, carboxin, fenpiclonil, 4-(2,2-difluoro-1,3-benzodioxol-4-yl)-1H-pyrrole-3-carbonitrile, butenafine, imazalil, N-methyl-isothiazolin-3-one, 5-chloro-N-methylisothiazolin-3-one, N-octylisothiazolin-3-one, benzisothiazolinone, N-(2-hydroxypropyl)-aminomethanol, benzyl alcohol (hemi)-formal, glutaraldehyde, omadine, dimethyl dicarbonate, and/or 3-iodo-2-propinyl n-butylcarbamate.

Furthermore, highly active mixtures are also prepared containing the following active compounds:

Fungicides:

acypetacs, 2-aminobutane, ampropylfos, anilazine, benalaxyl, bupirimate, chinomethionate, chloroneb, chlozolinate, cymoxanil, dazomet, diclomezine, dichloram, diethofencarb, dimethirimol, diocab, dithianone, dodine, drazoxolon, edifenphos, ethirimol, etridiazole, fenarimol, fenitropan, fentin acetate, fentin hydroxide, ferimzone, fluazinam, fluromide, flusulphamide, flutriafol, fosetyl, fthalide, furalaxyl, guazatine, hymexazol, iprobenfos, iprodione, isoprothiolane, metalaxyl, ethasulfocarb, nitrothal-isopropyl, nuarimol, ofurace, oxadiyl, perfluorazoate, pencycuron, phosdiphen, pimaricin, piperalin, procymidone, propamocarb, propineb, pyrazophos, pyrifenox, pyroquilone, quintozene, tar oils, tecnazene, thicyofen, thiophanate-methyl, tolclofos-methyl, triazoxide, trichlamide, tricyclazole, triforine, vinclozolin.

Insecticides:

phosphoric esters, such as azinphos-ethyl, azinphos-methyl, α-1(4-chlorophenyl)-4-(O-ethyl, S-propyl) phosphoryloxy-pyrazole, chlorpyrifos, coumaphos, demeton, demeton-S-methyl, diazinon, dichlorvos, dimethoate, ethoate, ethoprophos, etrimfos, fenitrothion, fenthion, heptenophas, parathion, parathion-methyl, phosalone, phoxim, pirimiphos-ethyl, pirimiphos-methyl, profenofos, prothiofos, sulfprofos, triazophos and trichlorphon;

carbamates, such as aldicarb, bendiocarb, α-2-(1-methylpropyl)phenylmethylcarbamate, butocarboxim, butoxycarboxim, carbaryl, carbofuran, carbosulfan, cloethocarb, isoprocarb, methomyl, oxamyl, pirimicarb, promecarb, propoxur and thiodicarb;

organosilicon compounds, preferably dimethyl(phenyl) silyl-methyl 3-phenoxybenzyl ethers, such as dimethyl-(4-ethoxyphenyl)-silylmethyl 3-phenoxybenzyl ether or (dimethylphenyl)-silyl-methyl 2-phenoxy-6-pyridylmethyl ethers, such as dimethyl-(9-ethoxy-phenyl)-silylmethyl 2-phenoxy-6-pyridylmethyl ether or [(phenyl)-3-(3-phenoxyphenyl)-propyl](dimethyl)-silanes, such as (4-ethoxyphenyl)-[3-(4-fluoro-3-phenoxyphenyl-propyl] dimethylsilane, silafluofen;

pyrethroids such as allethrin, alphamethrin, bioresmethrin, byfenthrin, cycloprothrin, cyfluthrin, decamethrin, cyhalothrin, cypermethrin, deltamethrin, alpha-cyano-3-phenyl 2-methylbenzyl-2,2-dimethyl-3-(2-chloro-2-trifluoro-methylvinyl)cyclopropanecarboxylate, fenpropathrin, fenfluthrin, fenvalerate, flucythrinate, flumethrin, fluvalinate, permethrin, resmethrin and tralomethrin;

nitroimines and nitromethylenes, such as 1-[(6-chloro-3-pyridinyl)-methyl]-4,5-dihydro-N-nitro-1H-imidazol-2-amine(imidacloprid), N-[(6-chloro-3-pyridyl)methyl-]$N^2$-cyano-$N^1$-methylacetamide (NI-25);

abamectin, AC 303, 630, acephate, acrinathrin, alanycarb, aldoxycarb, aldrin, amitraz, azamethiphos, *Bacillus thuringiensis*, phosmet, phosphamidon, phosphine, prallethrin, propaphos, propetamphos, prothoate, pyraclofos, pyrethrins, pyridaben, pyridafenthion, pyriproxyfen, quinalphos, RH-7988, rotenone, sodium fluoride, sodium hexafluorosilicate, sulfotep, sulfuryl fluoride, tar oils, teflubenzuron, tefluthrin, temephos, terbufos, tetrachlorvinphos, tetramethrin, O-2-tert-butyl-pyrimidin-5-yl o-isopropylphosphorothiate, thiocyclam, thiofanox, thiometon, tralomethrin, triflumuron, trimethacarb, vamidothion, *Verticillium lacanii*, XMC, xylylcarb, benfuracarb, bensultap, bifenthrin, bioallethrin, MERbioallethrin (S)-cyclopentenyl isomer, bromophos, bromophos-ethyl, buprofezin, cadusafos, calcium polysulfide, carbophenothion, cartap, quinomethionate, chlordane, chlorfenvinphos, chlorfluazuron, chlormephos, chloropicrin, chlorpyrifos, cyanophos, beta-cyfluthrin, alpha-cypermethrin, cyophenothrin, cyromazine, dazomet, DDT, demeton-S-methylsulphone, diafenthiuron, dialifos, dicrotophos, diflubenzuron, dinoseb, deoxabenzofos, diaxacarb, disulfoton, DNOC, empenthrin, endosulfan, EPN, esfenvalerate, ethiofencarb, ethion, etofenprox, fenobucarb, fenoxycarb, fensulfothion, fipronil, flucycloxuron, flufenprox, flufenoxuron, fonofos, formetanate, formothion, fosmethilan, furathiocarb, heptachlor, hexaflumuron, hydramethylnon, hydrogen cyanide, hydroprene, IPSP, isazofos, isofenphos, isoprothiolane, isoxathion, iodfenphos, kadethrin, lindane, malathion, mecarbam, mephosfolan, mercurous, chloride, metam, metarthizium, anisopliae, methacrifos, methamidophos, methidiathon, methiocarb, methoprene, methoxychlor, methyl isothiocyanate, metholcarb, mevinphos, monocrotophos, naled, neodiprion sertifer NPV, nicotine, omethoate, oxydemeton-methyl, pentachlorophenol, petroleum oils, phenothrin, phenthoate, phorate;

Molluscicides:

fentinacetate, metaldehyde, methiocarb, niclosamide, thiodicarb, trimethacarb.

Algicides:

copper sulphate, dichlororphen, endothal, fentinacetate, quinoclamine.

Herbicides:

acetochlor, acifluorfen, aclonifen, acrolein, alachlor, alloxydim, ametryn, amidosulfuron, amitrole, ammonium sulfamate, anilofos, asulam atrazine, aziptrotryne, benazolin, benfluralin, benfuresate, bensulfuron, bensulfide, bentazone, benzofencap, benzthiazuron, bifenox, bilanafos, borax, dichlorprop, dichlorprop-P, diclofop, diethatyl, difenoxuron, difenzoquat, diflufenican, dimefinon, dimepiperate, dimethachlor, dimethametryn, dimethipin, dimethylarsinic acid, dinitramine, dinoseb, dinoseb, dinoseb acetate, dinoseb, bromacil, bromobutide, bromofenoxim, bromoxynil, butachlor, butamifos, fuenachlor, butralin, butylate, carbetamide, CGA 184927, chlormethoxyfen, chloramben, chlorbromuron, chlorbutam, chlorfurenol, chloridazon, chlorimuron, chlornitrofen, chloroacetic acid, achloropicrin, chlorotoluron, chloroxuron, chlorprepham, chlorsulfuron, chlorthal, chlorthiamid, cinmethylin, cinofulsuron, clethodim, clomazone, clomeprop, clopyralid, cyanamide, cyanazine, dinoseb acetate, dinoterb, diphenamid, dipropetryn, diquat, dithiopyr, diduron, DNOC, PPX-A 788, DPX-E96361, DSMA, eglinazine, endothal, EPTC, esprocarb, ethalfluralin, ethidimuron, ethofumesate, fenoxaprop, fenoxaprop-P, fenuron, flamprop, flamprop-M, flazasulfuron, fluazifop, fluazifop-P, fluchloralin, flumeturon, fluorocgycofen, fluoronitrofen, flupropanate, flurenol, fluridone, flurochloridone, fluoroxypyr, cycloate, cycloxydim, 2,4-D, daimuron, dalapon, dazomet, 2,4-DB, desmedipham, desmetryn, dicamba, dichlorbenil, isoproturon, isouron, isoxaben, isoxapyrifop, lactofen, lenacil, linuron, LS830556, MCPA, MCPA-thioethyl, MCPB, mecoprop, mecoprop-P, mefenacet, mefluidide, metam, metamitron, metazachlor, methabenzthiazuron, methazole, methoproptryne, methyldymron, methyl isothiocyanate, metobromuron, fomosafen, fosamine, furyloxyfen, glufosinate, glyphosate, haloxyfop, hexazinone, imazamethabenz, imazapyr, imazaquin, imazethapyr, ioxynil, isopropalin, propyzamide, prosulfocab, pyrazolynate, pyrazolsulfuron, pyrazoxyfen, pyributicarb, pyridate, quinclorac, quiumerac, quinocloamine, quizalofop, quzizalofop-P, S-23121, sethoxydim, sifuron, simazine, simetryn, SMY 1500, sodium chlorate, sulfometuron, tar oils, TCA, metolachlor, metoxuron, metribzin, metsulfuron, molinate, monoalide, monolinuron, MSMA, naproanilide, napropamide, naptalam, neburon, nicosulfuron, nipyraclofen, norflurazon, orbencarb, oaryzalin, oxadiazon, oxyfluorfen, paraquat, pebulate, pendimethalin, pentachlorophenol, pentaochlor, petroleum oils, phenmedipham, picloram, piperophos, pretilachlor, primisulfuron, prodiamine, proglinazine, propmeton, prometryn, propachlor, tebutam, tebuthiuron, terbacil, terbumeton, terbuthylazine, terbutryn, thiazafluoron, thifensulfuron, thiobencarb, thiocarbazil, tioclorim, tralkoxydim, tri-allate, triasulfuron, tribenzuron, triclopyr, tridiphane, trietazine, trifluralin, IBI-C4874 vernolate, propanil, propaquizafop, propazine, propham.

The weight ratios of the active compounds in these active compound combinations can be varied in relatively large ranges.

Preferably, the active compound combinations contain the active compound at 0.1 to 99.9%, in particular at 1 to 75%, particularly preferably 5 to 50%, the remainder up to 100% being made up by one or more of the abovementioned mixing partners.

The microbicidal compositions or concentrates used to protect the technical materials contain the active compound or the active compound combination at a concentration of 0.01 and 95% by weight, in particular 0.1 to 60% by weight.

The application concentrations of the active compound to be used or of the active compound combination to be used depend on the type and occurrence of the microorganisms to be controlled and on the composition of the material to be protected. The optimal usage rate can be determined by test strips.

Generally, the application concentrations are in the range from 0.001 to 5% by weight, preferably from 0.05 to 1.0% by weight, based on the material to be protected.

The active compounds or compositions of the invention enable, in an advantageous manner, the microbicidal compositions available to date to be replaced by more effective ones. They show good stability and advantageously have a broad action spectrum.

The following examples serve to illustrate the invention. The invention is not restricted to the examples.

PREPARATION EXAMPLES

Example 1

(Precursor of the Formula (II))

10.3 g (0.06 mol) of ethyl α-formyl-hexanoate and 5.5 g (0.06 mol): of thiosemicarbazide are introduced into 200 ml of ethanol and stirred for 3 hours at 80° C.

The mixture is then brought to room temperature and 6.9 g of potassium tert-butoxide are added with stirring, in order to stir the mixture for a further 4 hours at room temperature. The contents of the flask are then stirred into a mixture of 800 ml of water and 50 ml of concentrated hydrochloric acid and the resulting precipitate is filtered off by suction. After thorough washing with water, the product is left in the drying cabinet until constant weight. The compound can be purified by recrystallization from ethanol.

Yield: 9.4 g (80.3% of theory)

m.p.: 139°–141° C.

(Final Stage of Formula (I))

26.48 g (0.236 mol) of potassium tert-butoxide are added to 47.1 g (0.236 mol) of the precursor in 450 ml of tetrahydrofuran at 25° C. After cooling to 0° C., 30 ml of 50% chloroacetaldehyde are added dropwise and the mixture is stirred for 16 hours at 25° C. After pouring the mixture into 750 ml of 10% HCl, it is extracted with methylene chloride, dried, the solvent is evaporated and the residue is stirred with diisopropyl ether.

26.1 g of the target compound I/007 of melting point 89°–91° C. are obtained. Recrystallization maintains the melting point at 91° C.

The following compounds of the formula (I) are obtained by analogy with Example 1 and in accordance with the general descriptions, it being also possible here to prepare the workup of the precursor directly and to prepare the final stage economizing on base:

TABLE 1

$R^1 = R^2 = R^3 = H$

| Example No. | $R^4$ | m.p. |
|---|---|---|
| 1 | H— | |
| 2 | Me— | |
| 3 | Et— | |
| 4 | n-Pr— | |
| 5 | i-Pr— | |
| 6 | c-Pr— | |
| 7 | n-Bu— | 91° C. |
| 8 | i-Bu— | |
| 9 | s-Bu— | |
| 10 | t-Bu— | |
| 11 | n-C$_5$H$_{11}$ | |
| 12 | 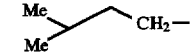 | |
| 13 | 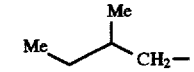 | |
| 14 | 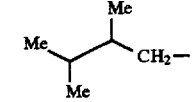 | |
| 15 | 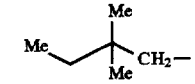 | |
| 16 | 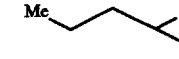 | |
| 17 | 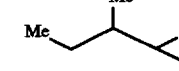 | |
| 18 | 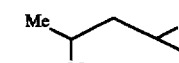 | |
| 19 | 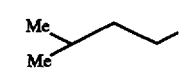 | |
| 20 |  | |
| 21 | 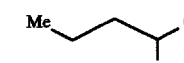 | |
| 22 | 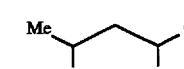 | |
| 23 | 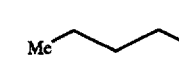 | |
| 24 | 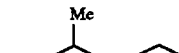 | |
| 25 | 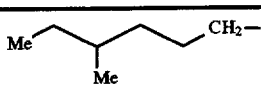 | |
| 26 | 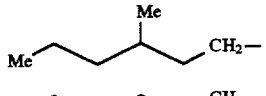 | |
| 27 |  | |
| 28 | 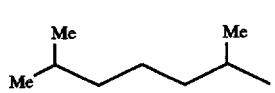 | |
| 29 | 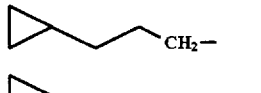 | |
| 30 |  | |
| 31 |  | |
| 32 | 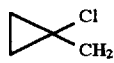 | |
| 33 | 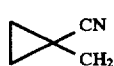 | |
| 34 | 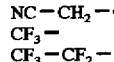 | |
| 35 | NC—CH$_2$—CH$_2$— | |
| 36 | CF$_3$— | |
| 37 | CF$_3$—CF$_2$— | |
| 38 | CF$_3$—CF$_2$—CF$_2$— | |
| 39 | CF$_2$—CF$_2$—CH$_2$— | |
| 40 | CF$_3$—CF$_2$—CF$_2$—CH$_2$— | |
| 41 | 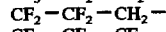 | 134–135° C. |
| 42 |  | |
| 43 |  | |
| 44 |  | |
| 45 |  | |
| 46 |  | |
| 47 | 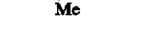 | |

TABLE 1-continued $R^1 = R^2 = R^3 = H$

| Example No. | R⁴ | m.p. |
|---|---|---|
| 48 | Me-C(Me)=CH-CH(Me)- | |
| 49 | Me-C(Me)=CH-CH₂- | |
| 50 | Me-CH=C(Me)-CH₂- | |
| 51 | Me-CH=C(Me)-CH₂- | |
| 52 | Me-C(Me)=CH-CH(Me)- | |
| 53 | Me-CH=CH-CH₂-CH₂- | |
| 54 | Me-C(Me)=CH-CH₂-CH₂- | |
| 55 | Me-CH=C(Me)-CH₂-CH₂- | |
| 56 | Me-CH₂-CH=C(Me)-CH₂- | |
| 57 | Me-CH₂-CH=C(Me)-CH₂- | |
| 58 | Me-CH₂-CH=CH-CH(Me)- | |
| 59 | Me-CH(Me)-CH=CH-CH(Me)- | |
| 60 | Me-C(Cl)=CH-CH₂- | |
| 61 | Cl-CH=C(Cl)-CH₂- | |
| 62 | Cl₂C=C(Cl)-CH₂- | |
| 63 | Me-C(Cl)=C(Me)-CH(Me)- | |
| 64 | Me-C(Cl)=C(Cl)-CH(Me)- | |
| 65 | Cl₂C=C(Cl)-CH(Me)- | |
| 66 | Cl₂C=CH-CH(Me)- | |
| 67 | Cl₂C=CH-CH₂-CH₂- | |
| 68 | Cl-CH=C(Cl)-CH₂-CH₂- | |
| 69 | Me-CH=C(Cl)-CH(Me)-CH₂- | |
| 70 | Me-C(Cl)=C(Cl)-CH₂-CH₂- | |
| 71 | Me-CH₂-C(Cl)=C(Cl)-CH₂-CH₂- | |
| 72 | Cl₂C=CH-CH₂-CH₂-CH₂- | |
| 73 | Cl-CH=C(Cl)-CH₂-CH₂-CH₂- | |
| 74 | Me-CH₂-C(Cl)=CH-CH₂- | |
| 75 | Me-CH₂-CH₂-CH=C(Cl)-CH₂- | |
| 76 | Me-CH=C(Cl)-CH₂-CH₂-CH(Me)- | |
| 77 | Me-C(Me)=CH-CH(Cl)-CH₂-CH₂-CH₂- | |
| 78 | n-C₇H₁₅ | |
| 79 | n-C₈H₁₇ | |
| 80 | n-C₉H₁₉ | |
| 81 | n-C₁₀—H₂₁ | |
| 82 | n-C₁₁H₂₃ | |
| 83 | n-C₁₂H₂₅ | |
| 84 | n-C₁₃H₂₇ | |
| 85 | cyclopentylmethyl | |

TABLE 1-continued $R^1 = R^2 = R^3 = H$

| Example No. | R⁴ | m.p. |
|---|---|---|
| 86 | cyclopent-2-enyl | |
| 87 | cyclopent-3-enyl | |
| 88 | cyclopentyl-CH₂— | |
| 89 | cyclopent-2-enyl-CH₂— | |
| 90 | cyclopent-3-enyl-CH₂— | |
| 91 | cyclohexyl | |
| 92 | cyclohex-2-enyl | |
| 93 | cyclohexyl-CH₂— | |
| 94 | cyclohex-3-enyl-CH₂— | |
| 95 | 3-(CO₂Et)-phenyl | |
| 96 | phenyl | |
| 97 | 2-Cl-phenyl | |
| 98 | 3-Cl-phenyl | |
| 99 | 4-Cl-phenyl | |
| 100 | 2,4-diCl-phenyl | |
| 101 | 2,3-diCl-phenyl | |
| 102 | 3,4-diCl-phenyl | |
| 103 | 2,5-diCl-phenyl | |
| 104 | 2,6-diCl-phenyl | |
| 105 | 2-F-phenyl | |
| 106 | 4-Br-phenyl | |
| 107 | 4-F-2-Me-phenyl | |
| 108 | 4-I-phenyl | |
| 109 | 2-CF₃-phenyl | |

TABLE 1-continued

R¹ = R² = R³ = H

| Example No. | R⁴ | m.p. |
|---|---|---|
| 110 | 2-MeO-C₆H₄ | |
| 111 | 3-MeO-C₆H₄ | |
| 112 | 4-MeO-C₆H₄ | |
| 113 | 3,4-(MeO)₂-C₆H₃ | |
| 114 | 3,4-(MeO)₂-C₆H₃ (2,3-isomer) | |
| 115 | 3-MeO-4-Me-C₆H₃ | |
| 116 | 2-MeO-4-Me-C₆H₃ | |
| 117 | 4-biphenyl | |
| 118 | 2-biphenyl | |
| 119 | 1-naphthyl | |
| 120 | 2-naphthyl | |
| 121 | 2-Me-C₆H₄ | |
| 122 | 3-Me-C₆H₄ | |
| 123 | 4-Me-C₆H₄ | |
| 124 | 2,3-Me₂-C₆H₃ | |
| 125 | 2,5-Me₂-C₆H₃ | |
| 126 | 3,5-Me₂-C₆H₃ | |
| 127 | 2,6-Me₂-C₆H₃ | |
| 128 | 2,4-Me₂-C₆H₃ | |
| 129 | 3,5-Me₂-C₆H₃ | |

TABLE 1-continued $R^1 = R^2 = R^3 = H$

| Example No. | R⁴ | m.p. |
|---|---|---|
| 130 | C₆H₅-CH₂- | |
| 131 | 2-F-C₆H₄-CH₂- | |
| 132 | 2-Cl-C₆H₄-CH₂- | |
| 133 | 3-Cl-C₆H₄-CH₂- | |
| 134 | 4-Cl-C₆H₄-CH₂- | |
| 135 | 2,4-Cl₂-C₆H₃-CH₂- | |
| 136 | 2,3-Cl₂-C₆H₃-CH₂- | |
| 137 | 3,4-Cl₂-C₆H₃-CH₂- | |
| 138 | 3,5-Cl₂-C₆H₃-CH₂- | |
| 139 | 2,5-Cl₂-C₆H₃-CH₂- | |
| 140 | 2,6-Cl₂-C₆H₃-CH₂- | |
| 141 | 4-Me-C₆H₄-CH₂- | |
| 142 | 3-Me-C₆H₄-CH₂- | |
| 143 | 2-Me-C₆H₄-CH₂- | |
| 144 | 2-OMe-C₆H₄-CH₂- | |
| 145 | 3-OMe-C₆H₄-CH₂- | |
| 146 | 4-MeO-C₆H₄-CH₂- | |
| 147 | 4-Bu-C₆H₄-CH₂- | |
| 148 | C₆H₅-CH(Me)- | |
| 149 | 4-Cl-C₆H₄-CH(Me)- | |
| 150 | 1-naphthyl-CH₂- | |
| 151 | 2-naphthyl-CH₂- | |
| 152 | C₆H₅-S- | |
| 153 | 4-Cl-C₆H₄-S- | |

TABLE 1-continued $R^1 = R^2 = R^3 = H$

| Example No. | $R^4$ | m.p. |
|---|---|---|
| 154 | phenyl-O— | |
| 155 | 4-Cl-phenyl-O— | |
| 156 | phenyl-CH₂—S— | |
| 157 | phenyl-CH₂—O— | |
| 158 | 4-Cl-phenyl-CH₂—S— | |
| 159 | MeO-C(O)- (acetate, MeO–C(=O)–) | |
| 160 | EtO-C(O)- | |
| 161 | n-PrO-C(O)- | |
| 162 | n-BuO-C(O)- | |
| 163 | Me—O— | |
| 164 | Et—O— | |
| 165 | n-Pr—O— | |
| 166 | n-Bu—O— | |
| 167 | Me—S—CH₂— | |
| 168 | Et—S—CH₂— | |
| 169 | n-Pr—S—CH₂— | |
| 170 | n-Bu—S—CH₂— | |
| 171 | i-Pr—S—CH₂— | |
| 172 | n-C₅H₄—S—CH₂— | |
| 173 | Me—S—(CH₂)₂— | |
| 174 | Et—S—(CH₂)₂— | |
| 175 | n-Pr—S—(CH₂)₂— | |
| 176 | n-Bu—S—(CH₂)₂— | |
| 177 | Me—O—CH₂— | |
| 178 | Et—O—CH₂— | |
| 179 | n-Pr—O—CH₂— | |
| 180 | n-Bu—O—CH₂— | |
| 181 | N-Pr—O—CH₂— | |
| 182 | n-C₅H₄—O—CH₂— | |
| 183 | Me—O—(CH₂)₂— | |
| 184 | Et—O—(CH₂)₂— | |
| 185 | n-Pr—O—(CH₂)₂— | |
| 186 | n-Bu—O—(CH₂)₂— | |
| 187 | Ph—S—CH₂— | |
| 188 | Ph—O—CH₂— | |
| 189 | Ph—CH₂—S—CH₂— | |
| 190 | PH—CH₂O—CH₂— | |
| 191 | MeO-C(O)-CH₂— | |
| 192 | EtO-C(O)-CH₂— | |
| 193 | 4-F-phenyl— | |
| 194 | 2-furyl— | |
| 195 | 2-thienyl— | |
| 196 | 3-furyl— | |
| 197 | 3-thienyl— | |
| 198 | 5-Me-2-furyl— | |
| 199 | 5-Me-2-thienyl— | |
| 200 | 3-Cl-pyrazolyl— | |
| 201 | 4-Br-phenyl-CH₂— | |
| 202 | 2-Br-phenyl— | |
| 203 | 4-F-phenyl— | |

TABLE 1-continued $R^1 = R^2 = R^3 = H$

| Example No. | R⁴ | m.p. |
|---|---|---|
| 204 | 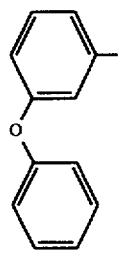 | |
| 205 | n-C₁₇—H₃₉ | |

TABLE II $R^1 = R^3 = H, R^2 = Me$

| Example No. | R⁴ | m.p. |
|---|---|---|
| 206 | H— | |
| 207 | Me— | |
| 208 | Et— | |
| 209 | n-Pr— | |
| 210 | i-Pr— | |
| 211 | c-Pr— | |
| 212 | n-Bu— | |
| 213 | i-Bu— | |
| 214 | s-Bu— | |
| 215 | t-Bu— | |
| 216 | n-C₅H₄ | |
| 217 | Me₂CH—CH₂— | |
| 218 | Me—CH(Me)—CH₂— (with additional Me) | |
| 219 | Me—CH(Me)—CH(Me)—CH₂— | |
| 220 | Me—C(Me)₂—CH₂— | |
| 221 | Me—CH₂—CH(Me)—Me | |
| 222 | Me—CH(Me)—CH(Me)—Me | |
| 223 | Me—CH(Me)—CH₂—CH(Me)—Me | |
| 24 | Me₂C—CH₂—CH₂—CH₂— | |
| 225 | Me—CH₂—CH(Me)—CH₂— | |

TABLE II-continued $R^1 = R^3 = H, R^2 = Me$

| Example No. | R⁴ | m.p. |
|---|---|---|
| 226 | Me—CH₂—CH(Me)—CH₂— | |
| 227 | Me—CH(Me)—CH₂—CH(Me)—CH₂— | |
| 228 | Me—(CH₂)₄—CH₂— | |
| 229 | Me₂CH—(CH₂)₃—CH₂— | |
| 230 | Me—CH₂—CH(Me)—CH₂—CH₂— | |
| 231 | Me—CH₂—CH(Me)—CH₂—CH₂— | |
| 232 | Me—(CH₂)₃—CH(Me)—CH₂— | |
| 233 | Me—(CH₂)₄—CH(Me)—Me | |
| 234 | Me—CH(Me)—(CH₂)₃—CH(Me)—Me | |
| 235 | cyclopropyl—CH₂—CH₂— | |
| 236 | cyclopropyl—CH₂— | |
| 237 | 1-F-cyclopropyl—CH₂— | |
| 238 | 1-Cl-cyclopropyl—CH₂— | |
| 239 | 1-CN-cyclopropyl—CH₂— | |
| 240 | NC—CH₂—CH₂— | |
| 241 | CF₃— | |
| 242 | CF₃—CF₂— | |
| 243 | CF₃—CF₂—CF₂— | |
| 244 | CF₂—CF₂—CH₂— | |
| 245 | CF₃—CF₂—CF₂—CH₂— | |
| 246 | CH₂=CH—CH₂— | |
| 247 | Me₂C=CH—CH₂— | |
| 248 | Me—C(Me)=CH—CH₂— | |

TABLE II-continued
R¹ = R³ = H, R² = Me
| Example No. | R⁴ | m.p. |
|---|---|---|
| 249 | 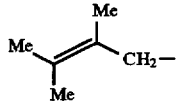 | |
| 250 | 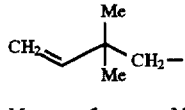 | |
| 251 |  | |
| 252 | 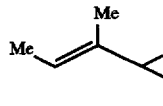 | |
| 253 | 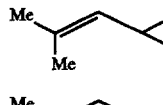 | |
| 254 | 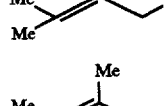 | |
| 255 | 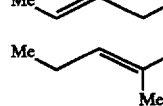 | |
| 256 | 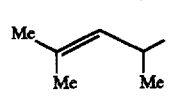 | |
| 257 | 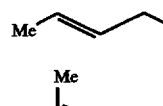 | |
| 258 | 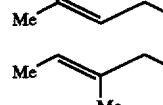 | |
| 259 | 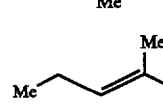 | |
| 260 | 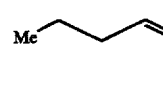 | |
| 261 | 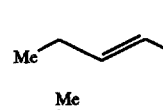 | |
| 262 | 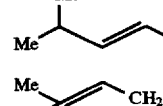 | |
| 263 | 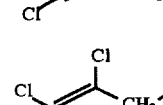 | |
| 264 | 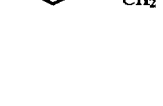 | |
| 265 |  | |
| 266 | 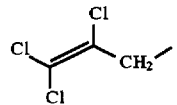 | |
| 267 | 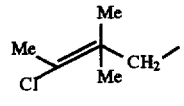 | |
| 268 | 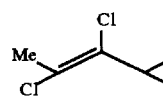 | |
| 269 | 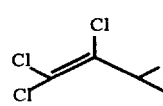 | |
| 270 | 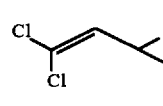 | |
| 271 | 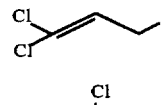 | |
| 272 | 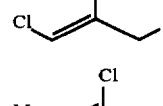 | |
| 273 | 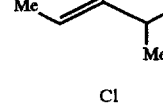 | |
| 274 | 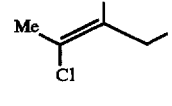 | |
| 275 | 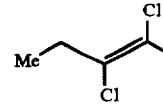 | |
| 276 | 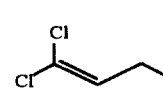 | |
| 277 | 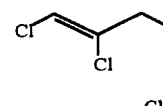 | |
| 278 | 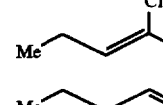 | |
| 279 |  | |
| 280 | 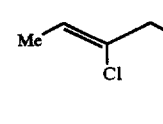 | |
| 281 | 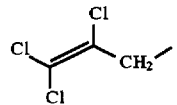 | |

TABLE II-continued $R^1 = R^3 = H, R^2 = Me$

| Example No. | R⁴ | m.p. |
|---|---|---|
| 282 | Me₂C=CH-CH(Cl)-CH₂-CH₂- | |
| 283 | n-C₇H₁₅ | |
| 284 | n-C₈H₁₇ | |
| 285 | n-C₉H₁₉ | |
| 286 | n-C₁₀—H₂₁ | |
| 287 | n-C₁₁H₂₃ | |
| 288 | n-C₁₂H₂₅ | |
| 289 | n-C₁₃H₂₇ | |
| 290 | cyclopentyl | |
| 291 | cyclopent-2-enyl | |
| 292 | cyclopent-3-enyl | |
| 293 | cyclopentylmethyl | |
| 294 | (cyclopent-2-enyl)methyl | |
| 295 | (cyclopent-3-enyl)methyl | |
| 296 | cyclohexyl | |
| 297 | cyclohex-2-enyl | |
| 298 | cyclohexylmethyl | |
| 299 | (cyclohex-2-enyl)methyl | |
| 300 | 3-(CO₂Et)-phenyl | |
| 301 | phenyl | oil |
| 302 | 2-Cl-phenyl | |
| 303 | 3-Cl-phenyl | |
| 304 | 4-Cl-phenyl | |
| 305 | 2,4-diCl-phenyl | |
| 306 | 2,3-diCl-phenyl | |
| 307 | 3,4-diCl-phenyl | |
| 308 | 2,5-diCl-phenyl | |
| 309 | 2,3-diCl-phenyl | |
| 310 | 2-F-phenyl | |
| 311 | 4-Br-phenyl | |

TABLE II-continued $R^1 = R^3 = H, R^2 = Me$

| Example No. | R⁴ | m.p. |
|---|---|---|
| 312 | 2-methyl-4-fluorophenyl | |
| 313 | 4-iodophenyl | |
| 314 | 2-(trifluoromethyl)phenyl | |
| 315 | 2-methoxyphenyl | |
| 316 | 3-methoxyphenyl | |
| 317 | 4-methoxyphenyl | |
| 318 | 3,4-dimethoxyphenyl | |
| 319 | 2,3-dimethoxyphenyl | |
| 320 | 2-methoxy-5-methylphenyl | |
| 321 | 3-methoxy-4-methylphenyl | |
| 322 | 4-biphenyl | |
| 323 | 2-biphenyl | |
| 324 | 1-naphthyl | |
| 325 | 2-naphthyl | |
| 326 | 2-methylphenyl | |
| 327 | 3-methylphenyl | |
| 328 | 4-methylphenyl | |
| 329 | 2,3-dimethylphenyl | |
| 330 | 2,5-dimethylphenyl | |
| 331 | 2,4-dimethylphenyl | |
| 332 | 2,6-dimethylphenyl | |

TABLE II-continued $R^1 = R^3 = H, R^2 = Me$

| Example No. | R⁴ | m.p. |
|---|---|---|
| 333 | 2,3-dimethylphenyl | |
| 334 | 3,5-dimethylphenyl | |
| 335 | benzyl (PhCH₂–) | |
| 336 | 2-F-C₆H₄-CH₂– | |
| 337 | 2-Cl-C₆H₄-CH₂– | |
| 338 | 3-Cl-C₆H₄-CH₂– | |
| 339 | 4-Cl-C₆H₄-CH₂– | |
| 340 | 2,4-Cl₂-C₆H₃-CH₂– | |
| 341 | 2,3-Cl₂-C₆H₃-CH₂– | |
| 342 | 3,4-Cl₂-C₆H₃-CH₂– | |
| 343 | 3,5-Cl₂-C₆H₃-CH₂– | |
| 344 | 2,5-Cl₂-C₆H₃-CH₂– | |
| 345 | 2,6-Cl₂-C₆H₃-CH₂– | |
| 346 | 4-Me-C₆H₄-CH₂– | |
| 347 | 3-Me-C₆H₄-CH₂– | |
| 348 | 2-Me-C₆H₄-CH₂– | |
| 349 | 2-OMe-C₆H₄-CH₂– | |
| 350 | 3-OMe-C₆H₄-CH₂– | |
| 351 | 4-MeO-C₆H₄-CH₂– | |
| 352 | 4-Bu-C₆H₄-CH₂– | |
| 353 | PhCH(Me)– | |
| 354 | 4-Cl-C₆H₄-CH(Me)– | |
| 355 | 1-naphthylmethyl (CH₂–) | |

TABLE II-continued $R^1 = R^3 = H, R^2 = Me$

| Example No. | R⁴ | m.p. |
|---|---|---|
| 356 | 2-naphthyl-CH₂— | |
| 357 | Ph—S— | |
| 358 | 4-Cl-C₆H₄—S— | |
| 359 | Ph—O— | |
| 360 | 4-Cl-C₆H₄—O— | |
| 361 | Ph—CH₂—S— | |
| 362 | Ph—CH₂—O— | |
| 363 | 4-Cl-C₆H₄—CH₂—S— | |
| 364 | MeO-C(O)— | |
| 365 | EtO-C(O)— | |
| 366 | n-PrO-C(O)— | |
| 367 | n-BuO-C(O)— | |
| 368 | Me—O— | |
| 369 | Et—O— | |
| 370 | n-Pr—O— | |
| 371 | n-Bu—O— | |
| 372 | Me—S—CH₂— | |
| 373 | Et—S—CH₂— | |
| 374 | n-Pr—S—CH₂— | |
| 375 | n-Bu—S—CH₂— | |
| 376 | i-Pr—S—CH₂— | |
| 377 | n-C₅H₄—S—CH₂— | |
| 378 | Me—S—(CH₂)₂— | |
| 379 | Et—S—(CH₂)₂— | |
| 380 | n-Pr—S—(CH₂)₂— | |
| 381 | n-Bu—S—(CH₂)₂— | |
| 382 | Me—O—CH₂— | |
| 383 | Et—O—CH₂— | |
| 384 | n-Pr—O—CH₂— | |
| 385 | n-Bu—O—CH₂— | |
| 386 | N-Pr—O—CH₂— | |
| 387 | n-C₅H₄—O—CH₂— | |
| 388 | Me—O—(CH₂)₂— | |
| 389 | Et—O—(CH₂)₂— | |
| 390 | n-Pr—O—(CH₂)₂— | |
| 391 | n-Bu—O—(CH₂)₂— | |
| 392 | Ph—S—CH₂— | |
| 393 | Ph—O—CH₂— | |
| 394 | Ph—CH₂—S—CH₂— | |
| 395 | PH—CH₂O—CH₂— | |
| 396 | MeO-C(O)-CH₂— | |
| 397 | EtO-C(O)-CH₂— | |
| 398 | 4-F-C₆H₄— | |
| 399 | 2-furyl— | |
| 400 | 2-thienyl— | |
| 401 | 3-furyl— | |
| 402 | 3-thienyl— | |
| 403 | 5-Me-2-furyl (Me substituent) | |
| 404 | 5-Me-2-thienyl (Me substituent) | |
| 405 | 3-Cl-pyrazolyl | |
| 406 | 4-Br-C₆H₄—CH₂— | |
| 407 | 2-Br-C₆H₄— | |

TABLE II-continued $R^1 = R^3 = H, R^2 = Me$

| Example No. | R⁴ | m.p. |
|---|---|---|
| 408 | 4-F-C₆H₄- | |
| 409 | 3-PhO-C₆H₄- | |
| 410 | n-C₁₇—H₃₉ | |

TABLE III $R^1 = R^2 = Me, R^3 = H$

| Example No. | R⁴ | m.p. |
|---|---|---|
| 411 | H— | |
| 412 | Me— | |
| 413 | Et— | |
| 414 | n-Pr— | |
| 415 | i-Pr— | |
| 416 | c-Pr— | |
| 417 | n-Bu— | |
| 418 | i-Bu | |
| 419 | s-Bu— | |
| 420 | t-Bu— | |
| 421 | n-C₅H₄ | |
| 422 | (Me)₂CH-CH₂- | |
| 423 | Me-CH₂-CH(Me)-CH₂- | |
| 424 | Me-CH(Me)-CH(Me)-CH₂- | |
| 425 | Me-CH₂-C(Me)₂-CH₂- | |
| 426 | Me-CH₂-CH₂-CH(Me)-Me | |
| 427 | Me-CH₂-CH(Me)-CH(Me)-Me | |
| 428 | Me-CH(Me)-CH₂-CH(Me)-Me | |
| 429 | (Me)₂CH-CH₂-CH₂-CH₂- | |
| 430 | Me-CH₂-CH(Me)-CH₂- | |
| 431 | Me-CH₂-CH₂-CH(Me)-CH₂- | |
| 432 | Me-CH(Me)-CH(Me)-CH(Me)-CH₂- | |
| 433 | Me-(CH₂)₃-CH₂- (n-pentyl chain) | |
| 434 | Me-CH(Me)-(CH₂)₂-CH₂- | |
| 435 | Me-CH₂-CH(Me)-CH₂-CH₂- | |
| 436 | Me-CH₂-CH(Me)-CH₂-CH₂- | |
| 437 | Me-CH₂-CH₂-CH(Me)-CH₂- | |
| 438 | Me-CH₂-CH₂-CH₂-CH(Me)-Me | |
| 439 | Me-CH(Me)-(CH₂)₃-CH(Me)-Me | |
| 440 | c-Pr-CH₂-CH₂- | |
| 441 | c-Pr-CH₂- | |
| 442 | 1-F-c-Pr-CH₂- | |
| 443 | 1-Cl-c-Pr-CH₂- | |
| 444 | 1-CN-c-Pr-CH₂- | |
| 445 | NC—CH₂—CH₂— | |
| 446 | CF₃— | |
| 447 | CF₃—CF₂— | |
| 448 | CF₃—CF₂—CF₂— | |
| 449 | CF₂—CF₂—CH₂— | |
| 450 | CF₃—CF₂—CF₂—CH₂— | |
| 451 | CH₂=CH-CH₂- | |
| 452 | (Me)₂C=CH-CH₂- | |
| 453 | Me-C(Me)=CH-CH₂- (Me on double bond) | |

TABLE III-continued
$R^1 = R^2 = Me, R^3 = H$
| Example No. | R⁴ | m.p. |
|---|---|---|
| 454 | 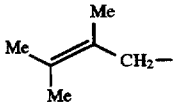 | |
| 455 | 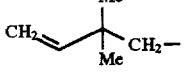 | |
| 456 | 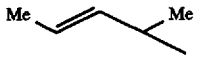 | |
| 457 | 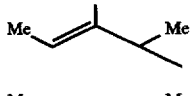 | |
| 458 | 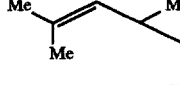 | |
| 459 | 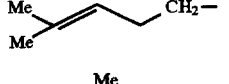 | |
| 460 | 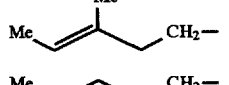 | |
| 461 | 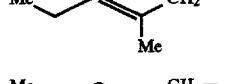 | |
| 462 | 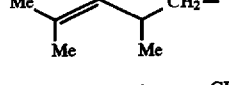 | |
| 463 | 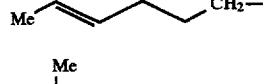 | |
| 464 | 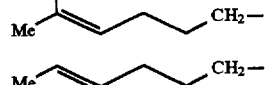 | |
| 465 | 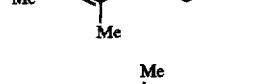 | |
| 466 | 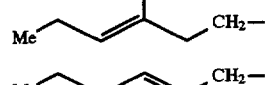 | |
| 467 | 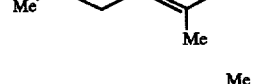 | |
| 468 | 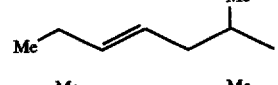 | |
| 469 | 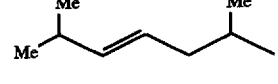 | |
| 470 | 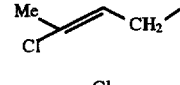 | |
| 471 | 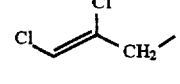 | |
| 472 | 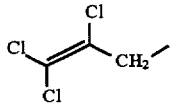 | |
| 473 | 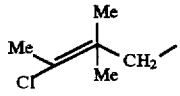 | |
| 474 | 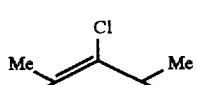 | |
| 475 | 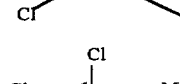 | |
| 476 | 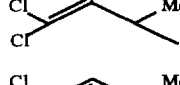 | |
| 477 | 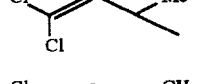 | |
| 478 | 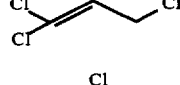 | |
| 479 | 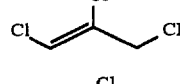 | |
| 480 | 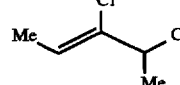 | |
| 481 | 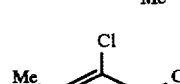 | |
| 482 | 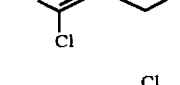 | |
| 483 | 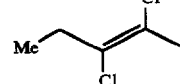 | |
| 484 | 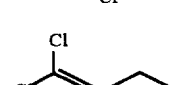 | |
| 485 | 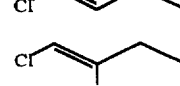 | |
| 486 | 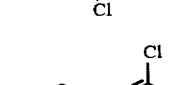 | |

TABLE III-continued

R¹ = R² = Me, R³ = H

| Example No. | R⁴ | m.p. |
|---|---|---|
| 487 | 2-methyl-4-chloro-hex-2-enyl (Me₂C=CH-CHCl-CH₂CH₂-) | |
| 488 | n-C₇H₁₅ | |
| 489 | n-C₈H₁₇ | |
| 490 | n-C₉H₁₉ | |
| 491 | n-C₁₀—H₂₁ | |
| 492 | n-C₁₁H₂₃ | |
| 493 | n-C₁₂H₂₅ | |
| 494 | n-C₁₃H₂₇ | |
| 495 | cyclopentyl | |
| 496 | cyclopentenyl | |
| 497 | cyclopentadienyl | |
| 498 | cyclopentyl-CH₂— | |
| 499 | cyclopentenyl-CH₂— | |
| 500 | cyclopentadienyl-CH₂— | |
| 501 | cyclohexyl | |
| 502 | cyclohexenyl | |
| 503 | cyclohexyl-CH₂— | |
| 504 | cyclohexenyl-CH₂— | |
| 505 | 3-(CO₂Et)-phenyl | |
| 506 | phenyl | |
| 507 | 2-Cl-phenyl | |
| 508 | 3-Cl-phenyl | |
| 509 | 4-Cl-phenyl | |
| 510 | 2,4-diCl-phenyl | |
| 511 | 2,3-diCl-phenyl | |
| 512 | 3,4-diCl-phenyl | |
| 513 | 2,5-diCl-phenyl | |
| 514 | 2,3-diCl-phenyl | |
| 515 | 2-F-phenyl | |
| 516 | 4-Br-phenyl | |

TABLE III-continued $R^1 = R^2 = Me, R^3 = H$

| Example No. | $R^4$ | m.p. |
|---|---|---|
| 517 | 4-F, 2-Me-phenyl | |
| 518 | 4-I-phenyl | |
| 519 | 2-CF$_3$-phenyl | |
| 520 | 2-OMe-phenyl | |
| 521 | 3-MeO-phenyl | |
| 522 | 4-MeO-phenyl | |
| 523 | 3,4-di-OMe-phenyl | |
| 524 | 3,4-di-MeO-phenyl | |
| 525 | 2-MeO, 5-Me-phenyl | |
| 526 | 2-OMe, 4-Me-phenyl | |
| 527 | 4-biphenyl | |
| 528 | 2-biphenyl | |
| 529 | 1-naphthyl | |
| 530 | 2-naphthyl | |
| 531 | 2-Me-phenyl | |
| 532 | 3-Me-phenyl | |
| 533 | 4-Me-phenyl | |
| 534 | 2,3-di-Me-phenyl | |
| 535 | 2,5-di-Me-phenyl | |
| 536 | 2,4-di-Me-phenyl | |
| 537 | 2,6-di-Me-phenyl | |

TABLE III-continued $R^1 = R^2 = Me, R^3 = H$

| Example No. | R⁴ | m.p. |
|---|---|---|
| 538 | 2,4-dimethylphenyl | |
| 539 | 3,5-dimethylphenyl | |
| 540 | benzyl (PhCH₂—) | 162–163° C. |
| 541 | 2-F-benzyl | |
| 542 | 2-Cl-benzyl | |
| 543 | 3-Cl-benzyl | |
| 544 | 4-Cl-benzyl | |
| 545 | 2,4-diCl-benzyl | |
| 546 | 2,3-diCl-benzyl | |
| 547 | 3,4-diCl-benzyl | |
| 548 | 3,5-diCl-benzyl | |
| 549 | 2,5-diCl-benzyl | |
| 550 | 2,6-diCl-benzyl | |
| 551 | 4-Me-benzyl | |
| 552 | 3-Me-benzyl | |
| 553 | 2-Me-benzyl | |
| 554 | 2-OMe-benzyl | |
| 555 | 3-OMe-benzyl | |
| 556 | 4-OMe-benzyl | |
| 557 | 4-Bu-benzyl | |
| 558 | PhCH(Me)— | |
| 559 | 4-Cl-PhCH(Me)— | |
| 560 | 1-naphthylmethyl | |

TABLE III-continued

R¹ = R² = Me, R³ = H

| Example No. | R⁴ | m.p. |
|---|---|---|
| 561 | 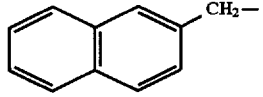 (2-naphthyl-CH₂—) | |
| 562 | 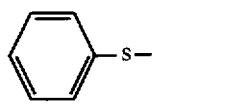 (Ph–S—) | |
| 563 | 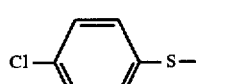 (4-Cl-C₆H₄–S—) | |
| 564 | 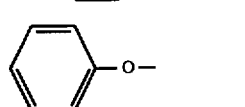 (Ph–O—) | |
| 565 | 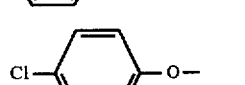 (4-Cl-C₆H₄–O—) | |
| 566 | 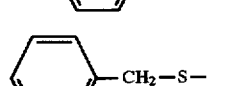 (Ph–CH₂–S—) | |
| 567 |  (Ph–CH₂–O—) | |
| 568 |  (4-Cl-C₆H₄–CH₂–S—) | |
| 569 | 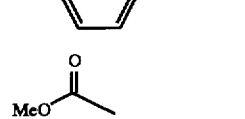 (MeO-C(=O)—) | |
| 570 |  (EtO-C(=O)—) | |
| 571 |  (n-PrO-C(=O)—) | |
| 572 | 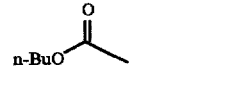 (n-BuO-C(=O)—) | |
| 573 | Me—O— | |
| 574 | Et—O— | |
| 575 | n-Pr—O— | |
| 576 | n-Bu—O— | |
| 577 | Me—S—CH₂— | |
| 578 | Et—S—CH₂— | |
| 579 | n-Pr—S—CH₂— | |
| 580 | n-Bu—S—CH₂— | |
| 581 | i-Pr—S—CH₂— | |
| 582 | n-C₅H₄—S—CH₂— | |
| 583 | Me—S—(CH₂)₂— | |
| 584 | Et—S—(CH₂)₂— | |
| 585 | n-Pr—S—(CH₂)₂— | |
| 586 | n-Bu—S—(CH₂)₂— | |
| 587 | Me—O—CH₂— | |

TABLE III-continued

R¹ = R² = Me, R³ = H

| Example No. | R⁴ | m.p. |
|---|---|---|
| 588 | Et—O—CH₂— | |
| 589 | n-Pr—O—CH₂— | |
| 590 | n-Bu—O—CH₂— | |
| 591 | n-Pr—O—CH₂— | |
| 592 | n-C₅H₄—O—CH₂— | |
| 593 | Me—O—(CH₂)₂— | |
| 594 | Et—O—(CH₂)₂— | |
| 595 | n-Pr—O—(CH₂)₂— | |
| 596 | n-Bu—O—(CH₂)₂— | |
| 597 | Ph—S—CH₂— | |
| 598 | Ph—O—CH₂— | |
| 599 | Ph—CH₂—S—CH₂— | |
| 600 | PH—CH₂—O—CH₂— | |
| 601 | 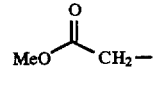 (MeO-C(=O)-CH₂—) | |
| 602 | 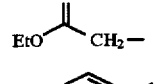 (EtO-C(=O)-CH₂—) | |
| 603 | 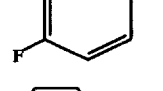 (4-F-C₆H₄—) | |
| 604 | 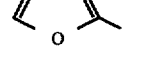 (2-furyl—) | |
| 605 | 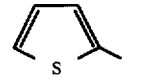 (2-thienyl—) | |
| 606 | 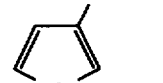 (3-furyl—) | |
| 607 | 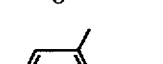 (3-thienyl—) | |
| 608 | 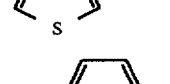 (2,5-dimethyl-3-furyl—) | |
| 609 | 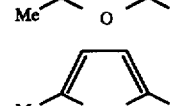 (2,5-dimethyl-3-thienyl—) | |
| 610 | 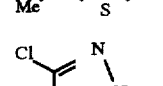 (3-chloro-pyrazol-1-yl—) | |
| 611 | 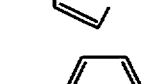 (4-Br-C₆H₄–CH₂—) | |
| 612 | 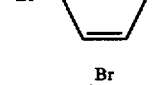 (2-Br-C₆H₄—) | |

TABLE III-continued

$R^1 = R^2 = Me, R^3 = H$

| Example No. | $R^4$ | m.p. |
|---|---|---|
| 613 | 4-F-C₆H₄— | |
| 614 | 3-(phenoxy)phenyl— | |
| 615 | n-C₁₇—H₃₉ | |

TABLE IV

$R^1 = R^2 = R^3 = Me$

| Example No. | $R^4$ | m.p. |
|---|---|---|
| 616 | H— | |
| 617 | Me— | |
| 618 | Et— | |
| 619 | n-Pr— | |
| 620 | i-Pr— | |
| 621 | c-Pr— | |
| 622 | n-Bu— | |
| 623 | i-Bu— | |
| 624 | s-Bu— | |
| 625 | t-Bu— | |
| 626 | n-C₅H₄ | |
| 627 | Me₂CH—CH₂— | |
| 628 | MeCH₂—CH(Me)—CH₂— | |
| 629 | MeCH(Me)—CH(Me)—CH₂— | |
| 630 | MeCH₂—C(Me)₂—CH₂— | |
| 631 | Me—CH₂—CH(Me)—Me | |
| 632 | Me—CH₂—CH(Me)—CH(Me)— | |
| 633 | Me—CH(Me)—CH(Me)—Me | |
| 634 | Me₂CH—CH₂—CH₂— | |

TABLE IV-continued

$R^1 = R^2 = R^3 = Me$

| Example No. | $R^4$ | m.p. |
|---|---|---|
| 635 | MeCH₂—CH(Me)—CH₂— | |
| 636 | MeCH₂—CH₂—CH(Me)—CH₂— | |
| 637 | MeCH(Me)—CH₂—CH(Me)—CH₂— | |
| 638 | Me—(CH₂)₄—CH₂— | |
| 639 | Me₂CH—(CH₂)₃—CH₂— | |
| 640 | MeCH₂—CH(Me)—CH₂—CH₂—CH₂— | |
| 641 | MeCH₂—CH₂—CH(Me)—CH₂—CH₂— | |
| 642 | MeCH₂—CH₂—CH₂—CH(Me)—CH₂— | |
| 643 | Me—(CH₂)₄—CH(Me)—Me | |
| 644 | Me₂CH—(CH₂)₃—CH(Me)—Me | |
| 645 | c-Pr—CH₂—CH₂—CH₂— | |
| 646 | c-Pr—CH₂— | |
| 647 | 1-F-c-Pr—CH₂— | |
| 648 | 1-Cl-c-Pr—CH₂— | |
| 649 | 1-CN-c-Pr—CH₂— | |
| 650 | NC—CH₂—CH₂— | |
| 651 | CF₃— | |
| 652 | CF₃—CF₂— | |
| 653 | CF₃—CF₂—CF₂— | |
| 654 | CF₂—CF₂—CH₂— | |
| 655 | CF₃—CF₂—CF₂—CH₂— | |
| 656 | CH₂=CH—CH₂— | |
| 657 | Me₂C=CH—CH₂— | |
| 658 | Me—CH=C(Me)—CH₂— | |

TABLE IV-continued
R¹ = R² = R³ = Me
| Example No. | R⁴ | m.p. |
|---|---|---|
| 659 | 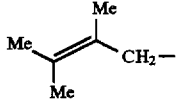 | |
| 660 | 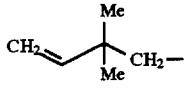 | |
| 661 | 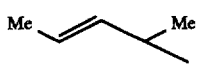 | |
| 662 | 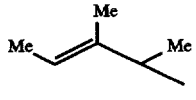 | |
| 663 | 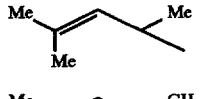 | |
| 664 | 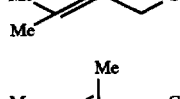 | |
| 665 | 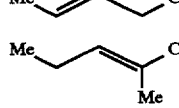 | |
| 666 | 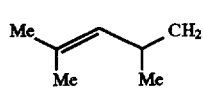 | |
| 667 | 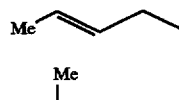 | |
| 668 | 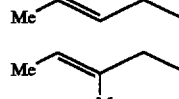 | |
| 669 | 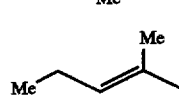 | |
| 670 | 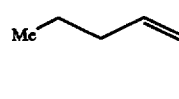 | |
| 671 | 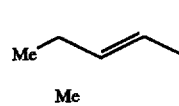 | |
| 672 | 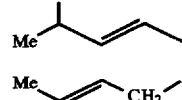 | |
| 673 | 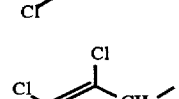 | |
| 674 |  | |
| 675 |  | |
| 676 | 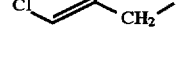 | |
| 677 | 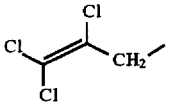 | |
| 678 | 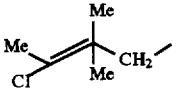 | |
| 679 | 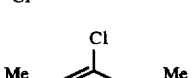 | |
| 680 | 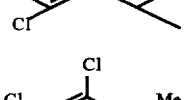 | |
| 681 | 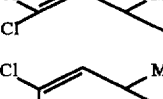 | |
| 682 | 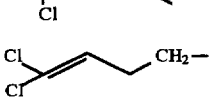 | |
| 683 | 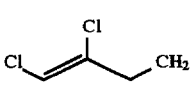 | |
| 684 | 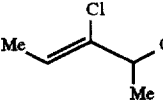 | |
| 685 | 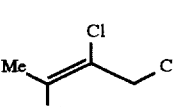 | |
| 686 | 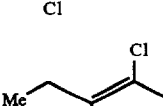 | |
| 687 | 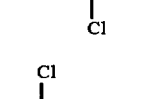 | |
| 688 | 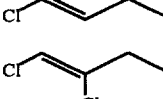 | |
| 689 | 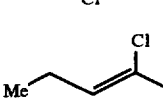 | |
| 690 | 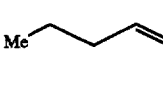 | |
| 691 | 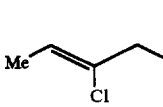 | |

TABLE IV-continued

| | $R^1 = R^2 = R^3 = Me$ | |
|---|---|---|
| Example No. | R⁴ | m.p. |
| 692 | CH(Me)=C(Me)–CH(Cl)–CH₂–CH₂–CH₂– (Me₂C=CH–CH(Cl)–CH₂CH₂CH₂–) | |
| 693 | n-C₇H₁₅ | |
| 694 | n-C₈H₁₇ | |
| 695 | n-C₉H₁₉ | |
| 696 | n-C₁₀—H₂₁ | |
| 697 | n-C₁₁H₂₃ | |
| 698 | n-C₁₂H₂₅ | |
| 699 | n-C₁₃H₂₇ | |
| 700 | cyclopentyl | |
| 701 | 2-cyclopentenyl | |
| 702 | 3-cyclopentenyl | |
| 703 | cyclopentylmethyl | |
| 704 | 2-cyclopentenylmethyl | |
| 705 | 3-cyclopentenylmethyl | |
| 706 | cyclohexyl | |
| 707 | cyclohexenyl | |
| 708 | cyclohexylmethyl | |
| 709 | cyclohexenylmethyl | |
| 710 | 3-(CO₂Et)-phenyl | |

TABLE IV-continued

| | $R^1 = R^2 = R^3 = Me$ | |
|---|---|---|
| Example No. | R⁴ | m.p. |
| 711 | phenyl | |
| 712 | 2-Cl-phenyl | |
| 713 | 3-Cl-phenyl | |
| 714 | 4-Cl-phenyl | |
| 715 | 2,4-di-Cl-phenyl | |
| 716 | 2,3-di-Cl-phenyl | |
| 717 | 3,4-di-Cl-phenyl | |
| 718 | 2,5-di-Cl-phenyl | |
| 719 | 2,3-di-Cl-phenyl (2,6-) | |
| 720 | 2-F-phenyl | |
| 721 | 4-Br-phenyl | |

TABLE IV-continued $R^1 = R^2 = R^3 = Me$

| Example No. | R⁴ | m.p. |
|---|---|---|
| 722 | 4-F, 2-Me-phenyl | |
| 723 | 4-I-phenyl | |
| 724 | 2-CF₃-phenyl | |
| 725 | 2-OMe-phenyl | |
| 726 | 3-MeO-phenyl | |
| 727 | 4-MeO-phenyl | |
| 728 | 3,4-(MeO)₂-phenyl | |
| 729 | 2,3-(MeO)₂-phenyl | |
| 730 | 2-MeO, 4-Me-phenyl | |
| 731 | 2-OMe, 4-Me-phenyl | |
| 732 | 4-biphenyl | |
| 733 | 2-biphenyl | |
| 734 | 1-naphthyl | |
| 735 | 2-naphthyl | |
| 736 | 2-Me-phenyl | |
| 737 | 3-Me-phenyl | |
| 738 | 4-Me-phenyl | |
| 739 | 2,3-Me₂-phenyl | |
| 740 | 2,4-Me₂-phenyl | |
| 741 | 2,4-Me₂-phenyl | |
| 742 | 2,6-Me₂-phenyl | |

TABLE IV-continued $R^1 = R^2 = R^3 = Me$

| Example No. | R⁴ | m.p. |
|---|---|---|
| 743 | 2,4-dimethylphenyl | |
| 744 | 3,5-dimethylphenyl | |
| 745 | benzyl (PhCH₂–) | |
| 746 | 2-F-benzyl | |
| 747 | 2-Cl-benzyl | |
| 748 | 3-Cl-benzyl | |
| 749 | 4-Cl-benzyl | |
| 750 | 2,4-diCl-benzyl | |
| 751 | 2,3-diCl-benzyl | |
| 752 | 3,4-diCl-benzyl | |
| 753 | 3,5-diCl-benzyl | |
| 754 | 2,5-diCl-benzyl | |
| 755 | 2,6-diCl-benzyl | |
| 756 | 4-Me-benzyl | |
| 757 | 3-Me-benzyl | |
| 758 | 2-Me-benzyl | |
| 759 | 2-OMe-benzyl | |
| 760 | 3-OMe-benzyl | |
| 761 | 4-OMe-benzyl | |
| 762 | 4-Bu-benzyl | |
| 763 | α-methylbenzyl (PhCH(Me)–) | |
| 764 | 4-Cl-α-methylbenzyl | |
| 765 | 1-naphthylmethyl | |

TABLE IV-continued

R¹ = R² = R³ = Me

| Example No. | R⁴ | m.p. |
|---|---|---|
| 766 | 2-naphthyl-CH₂— | |
| 767 | Ph—S— | |
| 768 | 4-Cl-C₆H₄—S— | |
| 769 | Ph—O— | |
| 770 | 4-Cl-C₆H₄—O— | |
| 771 | Ph—CH₂—S— | |
| 772 | Ph—CH₂—O— | |
| 773 | 4-Cl-C₆H₄—CH₂—S— | |
| 774 | MeO—C(O)— | |
| 775 | EtO—C(O)— | |
| 776 | n-PrO—C(O)— | |
| 777 | n-BuO—C(O)— | |
| 778 | Me—O— | |
| 779 | Et—O— | |
| 780 | n-Pr—O— | |
| 781 | n-Bu—O— | |
| 782 | Me—S—CH₂— | |
| 783 | Et—S—CH₂— | |
| 784 | n-Pr—S—CH₂— | |
| 785 | n-Bu—S—CH₂— | |
| 786 | i-Pr—S—CH₂— | |
| 787 | n-C₅H₄—S—CH₂— | |
| 788 | Me—S—(CH₂)₂— | |
| 789 | Et—S—(CH₂)₂— | |
| 790 | n-Pr—S—(CH₂)₂— | |
| 791 | n-Bu—S—(CH₂)₂— | |
| 792 | Me—O—CH₂— | |
| 793 | Et—O—CH₂— | |
| 794 | n-Pr—O—CH₂— | |
| 795 | n-Bu—O—CH₂— | |
| 796 | N-Pr—O—CH₂— | |
| 797 | n-C₅H₄—O—CH₂— | |
| 798 | Me—O—(CH₂)₂— | |
| 799 | Et—O—(CH₂)₂— | |
| 800 | n-Pr—O—(CH₂)₂— | |
| 801 | n-Bu—O—(CH₂)₂— | |
| 802 | Ph—S—CH₂— | |
| 803 | Ph—O—CH₂— | |
| 804 | Ph—CH₂—S—CH₂— | |
| 805 | PH—CH₂O—CH₂— | |
| 806 | 191  MeO—C(O)—CH₂— | |
| 807 | 192  EtO—C(O)—CH₂— | |
| 808 | 4-F-C₆H₄— | |
| 809 | 2-furyl— | |
| 810 | 2-thienyl— | |
| 811 | 3-furyl— | |
| 812 | 3-thienyl— | |
| 813 | 5-Me-2-furyl— | |
| 814 | 5-Me-2-thienyl— | |
| 815 | 3-Cl-pyrazol-1-yl— | |
| 816 | 4-Br-C₆H₄—CH₂— | |
| 817 | 2-Br-C₆H₄— | |

TABLE IV-continued

R¹ = R² = R³ = Me

| Example No. | R⁴ | m.p. |
|---|---|---|
| 818 | (4-F-phenyl) | |
| 819 | (3-phenoxyphenyl) | |
| 820 | n-C₁₇—H₃₉ | |

B. Testing the mould-resistance of coatings

The substance to be tested for its fungicidal activity is incorporated by means of a dissolver into the (emulsion) paint at the desired concentration. The paint is then brushed onto a suitable support on both sides.

In order to obtain results approximating those in practice, some of the test pieces are leached with flowing water (24 h; 20° C.) prior to the test for mould resistance.

The so prepared test pieces are placed on an agar nutrient medium. Test pieces and nutrient medium are infected with varieties of fungi. After storage for 1 to 3 weeks at 29°±1° C. and 80 to 90% relative humidity, the samples are inspected. The coating is permanently mould-resistant if the test piece remains free of fungus or if at most a slight marginal attack can be observed.

For the infection, fungal spores of the following nine moulds are used which are known as destroyers of coatings or are frequently encountered on coatings:

1. *Alternaria tenuis*
2. *Aspergillus flavus*
3. *Aspergillus niger*
4. *Aspergillus ustus*
5. *Cladosporium herbarum*
6. *Paecilomyces variotii*
7. *Penicillium citrinum*
8. *Aureobasidium pullulans*
9. *Stachybotrys atra Corda*

The following table V shows the active compound concentrations at which the coating test piece remains free of fungus (concentrations based on solids content of the emulsion paint).

Comparison example A: 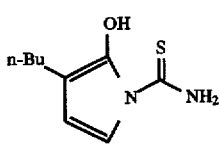

Comparison example B: 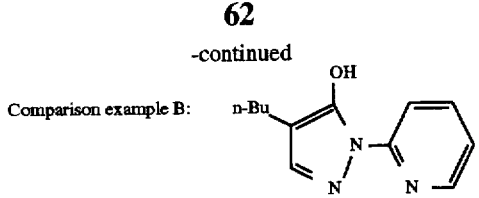

TABLE V

|  | without load | after watering | discoloration |
|---|---|---|---|
| Known Example A | 0.3% | >3% | none |
| Known Example B | 0.2% | 0.3% | from 0.3% |
| according to the invention Example 7 | 0.6% | 2.0% | none |

We claim:

1. Thiazolylpyrazolinone derivatives of the formula

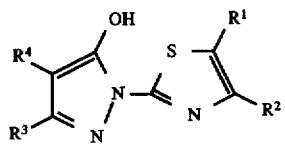

(I)

in which

R¹, R², R³ independently of each other each represent hydrogen, alkyl or halogen, and R⁴ represents hydrogen or unsubstituted or substituted alkyl, alkenyl, alkinyl, cycloalkyl, cycloalkenyl, alkyl (cycloalkyl), alkenyl (cycloalkenyl), alkoxy, alkylthio, aralkoxy, aralkylthio, aralkyl, aryl, hetaryl, aryloxy, hetaryloxy, arylthio, hetarylthio, alkoxycarbonyl, alkoxycarbonalalkyl or cyanoalkyl, or their acid addition products or metal complexes, wherein if R⁴ represents substituted hetaryl, then the substituents are selected from the group consisting of halogen, alkyl, alkoxy or alkylthio.

2. Compounds of the formula (I) according to claim 1, in which

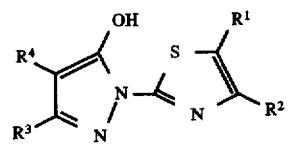

(I)

R¹, R², R³ denote hydrogen or methyl,

R⁴ denotes unsubstituted or substituted alkyl, cycloalkyl, alkenyl, aralkyl or aryl.

3. Compounds of the formula (I) according to claim 1, in which

R¹ denotes hydrogen,

R², R³ denote hydrogen or methyl,

R⁴ denotes unsubstituted or substituted alkyl, cycloalkyl, aralkyl or aryl.

4. Compounds of the formula (I) according to claim 1, in which

R¹, R² and R³ denote hydrogen,

R⁴ denotes unsubstituted or substituted alkyl or cycloalkyl.

5. Process for the preparation of novel thiazolylpyrazolinone derivatives of the formula (I) according to claim 1, characterized in that thiocarbamoyl compounds of the formula (II)

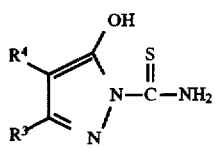

in which $R^3$ and $R^4$ have the meanings given above are reacted, in the presence or absence of a solvent or diluent and in the presence or absence of a base, with compounds of the formula (III)

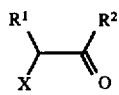

in which $R^1$ and $R^2$ have the meanings given above and X represents a leaving group.

6. A composition for protecting a technical material from attack and destruction by a microorganism comprising a protective effective amount of a compound of the formula (I) according to claim 1 and an extender.

7. A method of protecting a technical material from attack and destruction by a microorganism comprising applying to the technical material or admixing with the technical material a protective effective amount of a compound of the formula (I) according to claim 1.

* * * * *